United States Patent
Mihan et al.

(10) Patent No.: US 7,214,842 B2
(45) Date of Patent: May 8, 2007

(54) METHOD FOR OLIGOMERIZING OLEFINS

(75) Inventors: Shahram Mihan, Ludwigshafen (DE); Heiko Maas, Mannheim (DE); Martina Prinz, Dossenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 251 days.

(21) Appl. No.: 10/509,871

(22) PCT Filed: Apr. 9, 2003

(86) PCT No.: PCT/EP03/03691

§ 371 (c)(1),
(2), (4) Date: Oct. 1, 2004

(87) PCT Pub. No.: WO03/084902

PCT Pub. Date: Oct. 16, 2003

(65) Prior Publication Data

US 2005/0165266 A1    Jul. 28, 2005

(30) Foreign Application Priority Data

Apr. 10, 2002 (DE) .................. 102 15 754

(51) Int. Cl.
*C07C 2/02* (2006.01)
(52) U.S. Cl. ............... 585/523; 585/527; 585/532
(58) Field of Classification Search ........ 585/523, 585/527, 532; 526/78, 79
See application file for complete search history.

(56) References Cited

FOREIGN PATENT DOCUMENTS

| DE | 30 07 725 | 9/1981 |
|---|---|---|
| DE | 199 43 544 | 3/2001 |
| EP | 0 531 174 | 3/1993 |
| EP | 0 537 609 | 4/1993 |

OTHER PUBLICATIONS

Tani, Kazuhide et al. "Preparation of .alpha.-olefin polymers by the use of vanadium or chromium complex catalysts", STN Caplus, vol. 129, No. 18, XP002139725, English abstract only 1998.
Koide, Yoshihiro et al. "Alumoxanes as Cocatalysts in the Palladium-Catalyzed Copolymerization of Carbon Monoxide and Ethylene: Genesis of a Structure-Activity Relationship", Organometallics, vol. 15, pp. 2213-2226 1996.
Barron, Andrew R. "A New Understanding of the Co-Catalytic Activity of Alumoxanes: The Opening of a Black Box!", Macromol. Symp., vol. 97, pp. 15-25 1995.
Gladysz, J.A. "Frontiers in Metal-Catalyzed Polymerization: Designer Metallocenes, Designs on New Monomers, Demystifying MAO, Metathesis Deshabille", Chemical Reviews, vol. 100, No. 4, pp. 1167-1168 2000.
Ruether, Thomas et al. "Novel Chromium(III) Complexes Containing Imidazole-Based Chelate Ligands with Varying Donor Sets: Synthesis and Reactivity", Organometallics, vol. 20, pp. 1247-1250 2001.
Doehring, Amo et al. "Donor-Ligand-Substituted Cyclopentadienylchromium(III) Complexes: A New Class of Alkene Polymerization Catalyst. 2. Phosphinoalkyl-Subsituted Systems", Organometallics, vol. 20, pp. 2234-2245 2001.
Deckers, Patrick J.W. et al. "Switching a Catalyst System from Ethene Polymerization to Ethene Trimerization with a Hemilabile Ancillary Ligand", Angew. Chem., vol. 113, No. 13, pp. 2584-2587 2001.

*Primary Examiner*—Glenn Caldarola
*Assistant Examiner*—In Suk Bullock
(74) *Attorney, Agent, or Firm*—Oblon, Spivak, McClelland, Maier & Neustadt, P.C.

(57) ABSTRACT

Olefins are oligomerized by contacting an olefin with a catalyst system that is comprised of a) at least one transition metal complex that is complexed with a polydentate complexing ligand and b) an alkylaluminoxane, each component being present in such amounts that the molar ratio of aluminum transition metal is greater than 10, wherein at least part of the amount of the transition metal complex is added continuously or in portions during the oligomerization.

11 Claims, No Drawings

METHOD FOR OLIGOMERIZING OLEFINS

BACKGROUND OF THE INVENTION

1. Field of the Invention

The present invention relates to a process for the oligomerization of olefins, in which an olefin is brought into contact with a catalyst system comprising at least one transition metal complex with a polydentate complexing ligand and an alkylaluminoxane.

2. Description of the Background

Olefin oligomers having up to 30 carbon atoms have great economic importance as comonomers for plastics or as precursors for oxo alcohols which are in turn constituents of surfactants and plasticizers for plastics. Processes for the oligomerization of lower olefins produced in, for example, steam crackers are thus of central importance in the production of products used in daily life.

WO 00/58319 describes a process for preparing oligomers of olefins using an oligomerization catalyst which is obtainable from a chromium compound and a 1,3,5-triazacyclohexane and an activating additive such as an alkylaluminoxane.

EP-A-0 537 609 describes the oligomerization of ethene in the presence of a catalyst comprising a chromium complex with a polydentate complexing ligand and an alkylaluminoxane.

Although the mechanism of olefin oligomerization over transition metal complexes has not been fully elucidated, it is assumed that the "activation" of the transition metal complex by the alkylaluminoxane involves a ligand exchange reaction between an abstractable ligand of the complex and the alkyl group of the alkylaluminoxane. This forms a catalytically active species which adds on olefin molecules in a stepwise fashion. The olefin molecules react in the coordination sphere of the transition metal complex to form an oligomer. Liberation of the oligomer regenerates the catalytically active species. However, even with substantial exclusion of impurities, the catalytic activity of the catalyst system becomes exhausted after some time. In general, the catalyst system is then discarded.

The alkylaluminoxane is usually used in a large excess based on the transition metal complex in order to achieve satisfactory activation. The associated high consumption of alkylaluminoxane therefore represents a considerable cost factor in such olefin oligomerization processes.

SUMMARY OF THE INVENTION

It is an object of the present invention to provide a process for the oligomerization of olefins in which an olefin is brought into contact with a catalyst system comprising a transition metal complex and an alkylaluminoxane and which allows optimum utilization of the alkylaluminoxane.

We have found that this object is achieved by a process for the oligomerization of olefins, in which an olefin is brought into contact with a catalyst system comprising
a) at least one transition metal complex with a polydentate complexing ligand and
b) an alkylaluminoxane in such amounts that the molar ratio of aluminum:transition metal is greater than 10, where at least part of the amount of the transition metal complex is added continuously or in portions during the oligomerization.

DETAILED DESCRIPTION OF THE PREFERRED EMBODIMENTS

Suitable alkylaluminoxanes are, for example, known from DE-A-3 007 725, and their structures are largely unelucidated. They are products of the careful partial hydrolysis of aluminum alkyls. These products are obviously not in the form of pure chemical compounds, but are mixtures of open-chain and cyclic structures of the types Ia and Ib which are presumably in dynamic equilibrium with one another.

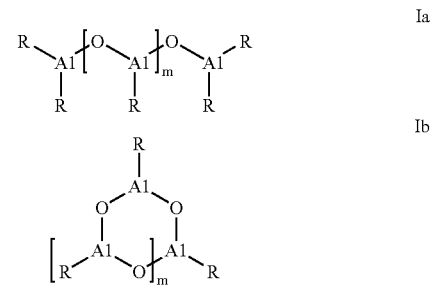

In the formulae Ia and Ib, the groups R are identical or different and are each, independently of one another, $C_1$–$C_{12}$-alkyl such as methyl, ethyl, n-propyl, i-propyl, n-butyl, i-butyl, sec-butyl, tert-butyl, n-pentyl, i-pentyl, sec-pentyl, neopentyl, 1,2-dimethylpropyl, i-amyl, n-hexyl, i-hexyl, sec-hexyl, n-heptyl, i-heptyl, n-octyl, n-nonyl, n-decyl and n-dodecyl; preferably $C_1$–$C_6$-alkyl such as methyl, ethyl, n-propyl, i-propyl, n-butyl, i-butyl, sec-butyl, tert-butyl, n-pentyl, i-pentyl, sec-pentyl, neopentyl, 1,2-dimethylpropyl, i-amyl, n-hexyl, i-hexyl. Methylaluminoxane is particularly preferred. m is an integer from 0 to 40, preferably from 0 to 25 and in particular from 0 to 22.

Cage-like structures for aluminoxanes have also been discussed in the literature (cf. *Organometallics* 1996, 15, pp. 2213–26; Makromol. Symp. 1995, 97, pp. 15–25).

The alkylaluminoxanes are suitable for the purposes of the present invention regardless of their structural nature.

The transition metal complex can be any complex which, after activation, is capable of oligomerizing olefins. Suitable catalysts of this type are described in "Frontiers in metal-catalyzed Polymerization", Chem. Rev. April 2000, Vol. 100, No. 4, pp. 1167–1645. The transition metal in preferred complexes is selected from among chromium, vanadium, tantalum and titanium.

Suitable transition metal complexes can be represented by the formula $LMeX_k$, where Me is a transition metal, preferably Cr, V or Ti, L is a polydentate complexing ligand, X are identical or different anions and k is 2 or 3.

The polydentate complexing ligand preferably occupies three adjacent coordination positions on the octahedrally coordinated metal atom. Nitrogen-containing polydentate complexing ligands are preferred. Particular preference is given to cyclic polyamine ligands, in particular ones having a 1,3,5-triazacyclohexane or a 1,4,7-triazacyclononane skeleton.

Suitable complexing ligands having a 1,3,5-triazacyclohexane skeleton are described in WO 00/58319, whose disclosure is hereby incorporated by reference. Among these, preference is given to 1,3,5-triazacyclohexanes whose nitrogen atoms are substituted independently of one another by substituted or unsubstituted $C_1$–$C_{12}$-alkyl, $C_6$–$C_{15}$-aryl or $C_7$–$C_{15}$-arylalkyl, e.g. by methyl, ethyl, N,N-dimethylaminoethyl, n-propyl, n-butyl, tert-butyl, hexyl, octyl, dodecyl, 1,1-dimethyldodecyl or 1-phenylethyl.

Preferred 1,3,5-triazacyclohexanes are 1,3,5-tri-tert-butyl-1,3,5-triazacyclohexane, 1,3,5-triethyl-1,3,5-triazacyclohexane, 1,3,5-tris[(1-phenylethyl)]-1,3,5-triazacyclohexane, 1,3,5-tris[(1,1-dimethyl)dodecyl]-1,3,5-triazacyclohexane and 1,3-di-n-dodecyl-5-[2-(N,N-dimethylamino)ethyl]-1,3,5-triazacyclohexane and also, particularly preferably, 1,3,5-tri-n-octyl-1,3,5-triazacyclohexane, 1,3,5-tri-n-dodecyl-1,3,5-triazacyclohexane, 1,3,5-tribenzyl-1,3,5-triazacyclohexane, 1,3,5-tris(2-ethylhexyl)-1,3,5-triazacyclohexane, 1,3,5-tris(2-n-propylheptyl)-1,3,5-triazacyclohexane.

Suitable 1,4,7-triazacyclononanes can be substituted on the nitrogen atoms by substituents as described above. 1,4,7-trimethyl-1,4,7-triazacyclononane is commercially available.

Alternative polydentate complexing ligands are cyclopentadienyl anions of the formula $C_5H_{(5-n)}R_n$ and their benzo-fused derivatives, where n is an integer from 0 to 5 and R is $C_1$–$C_6$-alkyl, $C_2$–$C_6$-alkenyl, $C_6$–$C_{10}$-aryl, $C_7$–$C_{14}$-aralkyl, $R^1_2P$—X— or $R^1_2N$—X—, where $R^1$ is $C_1$–$C_6$-alkyl, $C_5$–$C_6$-cycloalkyl or $C_6$–$C_{10}$-aryl and X is $C_1$–$C_6$-alkylene. n is preferably 1. Suitable cyclopentadienyl ligands are, for example,
2-di($C_1$–$C_6$-alkyl)phosphinoethylcyclopentadienyl,
3-di($C_1$–$C_6$-alkyl)phosphinopropylcyclopentadienyl,
2-di($C_1$–$C_6$-alkyl)aminoethylcyclopentadienyl,
t-butylcyclopentadienyl or 2-phenylprop-2-ylcyclopentadienyl.

Further alternative polydentate complexing ligands are bis(N-methylimidazol-2-yl) compounds of the formula

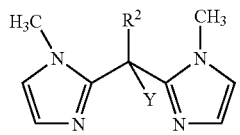

where $R^2$ is hydrogen, $C_1$–$C_6$-alkyl or $C_1$–$C_6$-alkoxy and Y is N-methylimidazol-2-yl, $R^1_2P$—X— or $R^1_2N$—X—, where $R^1$ is $C_1$–$C_6$-alkyl, $C_5$–$C_6$-cycloalkyl or $C_6$–$C_{10}$-alkyl and X is $C_1$–$C_6$-alkylene.

Suitable anions X are, in particular, halides such as fluoride, bromide, iodide and in particular chloride; tosylate, triflate, tetrafluoroborate, hexafluorophosphate, hexafluoroantimonate, tetraphenylborate; $C_1$–$C_{18}$-carboxylate such as acetate, butyrate, neopentanoate, laurate, stearate or 2-ethylhexanoate.

The transition metal complexes can be obtained by methods known to those skilled in the art or by methods analogous to these (e.g., for example, W. A. Herrmann, A. Salzer: "Synthetic Methods of Organometallic and Inorganic Chemistry", Thieme Verlag, Stuttgart 1996). Suitable complexes are described in WO 00/58319, EP-A-0 537 609, Rüther, T. et al., Organometallics 2001, 20, pp. 1247–1250; Döhring A. et al., Organometallics 2001, 20, pp. 2234–2245 and Deckers P. J. W. et al., Angew. Chem. 2001, 113, No. 13, pp. 2584–2587.

The transition metal complex and the alkylaluminoxane are used in such amounts that the molar ratio of aluminum:transition metal is greater than 10, e.g. from 10 to 10000, preferably from 10 to 500. According to the present invention, at least part of the amount of transition metal complex used is added continuously or in portions during the oligomerization, i.e. after olefin, alkylaluminoxane and a partial amount of the complex have been brought into contact under conditions under which oligomerization of the olefin occurs. In general, the total amount of alkylaluminoxane and a partial amount of the complex are combined in situ immediately before using the oligomerization reaction. The olefin to be oligomerized can likewise be initially charged and/or added continuously or in portions to the combined catalyst components. As an alternative, it is possible for the aluminoxane and the olefin to be initially charged and the first partial amount of the transition metal complex to be added.

During the course of the oligomerization, advantageously when the activity of the catalyst system has deteriorated appreciably, for example after a time of at least 30 minutes or 1 hour, a further partial amount of the transition metal complex can be added to the polymerizing system. This procedure can be repeated as often as desired, as long as the total amount of transition metal complex, i.e. the sum of initially charged and added partial amounts, and the amount of alkylaluminoxane present in the reaction system correspond to a molar ratio of aluminum:transition metal of greater than 10.

In a preferred embodiment, a partial amount of the transition metal complex is initially charged together with the alkylaluminoxane and the molar ratio of aluminum:transition metal is reduced to less than half of the initial value during the oligomerization by addition of at least one further partial amount of the transition metal complex. The initial molar ratio of aluminum:transition metal is advantageously greater than 100, preferably greater than 200, in particular greater than 300. In place of addition of the chromium complex in portions, the transition metal complex can also be metered in continuously during the oligomerization, for example to obtain a high catalyst activity over a relatively long period of time.

The method of carrying out the process according to the present invention makes it possible to obtain a significantly higher yield of olefin oligomer when using a given amount of aluminoxane.

The process of the present invention is generally carried out in the liquid phase in a solvent. Suitable solvents are aprotic solvents, e.g. aliphatic saturated hydrocarbons such as butane, pentane, 3-methylpentane, hexane, heptane, 2-methylhexane, octane, cyclohexane, methylcyclohexane, 2,2,4-trimethylpentane, decalin; halogenated hydrocarbons such as dichloroethane; aromatic hydrocarbons such as benzene, toluene, xylene, ethylbenzene, mesitylene, tetralin or the oligomeric reaction products which are liquid under the reaction conditions, e.g. 1-hexene. These solvents can be used either individually or as mixtures.

The process of the present invention is suitable for the oligomerization, in particular the selective trimerization, of ethene. The process of the present invention is also suitable for the oligomerization, in particular the selective trimerization, of α-olefins having at least three, e.g. from three to twelve, carbon atoms, e.g. 1-propene, 1-butene, 1-hexene, 1-decene. A particularly useful olefin is 1-butene, if desired in admixture with its isomers as are present, for example, in raffinate II.

Owing to the tendency of the alkylaluminoxane to undergo hydrolysis, the process of the present invention is generally carried out with substantial exclusion of moisture. Preference is given to carrying it out under protective gas. Protective gases which can be used are all gases which are chemically inert under the reaction conditions, e.g. nitrogen or argon. Furthermore, the olefin to be reacted can itself take on the function of protective gas if it has a sufficiently high vapor pressure under the reaction conditions.

The oligomerization is preferably carried out at from 0 to 120° C., in particular from 25 to 110° C. It is carried out at a pressure in the range from ambient pressure to 120 bar.

After the reaction is complete, the catalyst system is generally deactivated. Suitable deactivators are for example, water, which may be acidified, and lower alcohols. The products of the oligomerization are advantageously purified by distillation. Unreacted starting material can be recovered and returned to the reaction.

The invention is illustrated by the following examples.

EXAMPLE 42.1 µmol of (1,3,5-tris-n-dodecyl-1,3,5-triazacyclohexane)$CrCl_3$ together with 250 ml of toluene were placed under an argon atmosphere in a one liter four-necked flask provided with contact thermometer, stirrer, heating metal and gas inlet tube at 40° C. The solution was saturated with butene. 14.74 mmol of methylaluminoxane (MAO), corresponding to a molar ratio of aluminum:chromium of 350, were then added in the form of a 1.6 M solution in toluene. 1-butene was passed through the light-green/yellow solution obtained after the addition of the MAO. After one hour, a further 40.2 µmol of chromium complex were added, so that the molar ratio of aluminum:chromium was now 180. After a further hour, another 40.5 µmol of chromium complex were added and the molar ratio of aluminum:chromium was then 120. After a total of 3 hours, the reaction was stopped by addition of 15 ml of concentrated hydrochloric acid in 50 ml of methanol and the reaction mixture was stirred for another 15 minutes. 250 ml of methanol were then added and the mixture was stirred for a further 15 minutes. The product was washed three times with water and dried over sodium sulfate. The yield of dodecene was determined by gas-chromatographic analysis of the solution obtained in this way. A total of 25.8 g of dodecene had been formed.

COMPARATIAVE EXAMPLE 40.9 µmol of (1,3,5-tris-n-dodecyl-1,3,5-triazacyclohexane)$CrCl_3$ together with 250 ml of toluene were placed in a one liter four-necked flask provided with contact thermometer, stirrer, heating metal and gas inlet tube at 40° C. The solution was saturated with butene. 14.32 mmol of methylaluminoxane (MAO), corresponding to a molar ratio of aluminum:chromium of 350, were then added in the form of a 1.6 M solution in toluene. 1-butene was passed through the solution. After one hour, dodecene production decreased significantly. The work-up was carried out as described in the above example. 10.2 g of dodecene were obtained.

We claim:

1. A process for the oligomerization of olefins in which an olefin is brought into contact with a catalyst system, comprising:
   a) at least one transition metal complex with a polydentate complexing ligand and
   b) an alkylaluminoxane in such amounts that the molar ratio of aluminum:transition metal is greater than 10, wherein at least part of the amount of the transition metal complex is added continuously or in portions during the oligomerization.

2. The process as claimed in claim 1, wherein a partial amount of the transition metal complex is initially charged together with the alkylaluminoxane and the molar ratio of aluminum:transition metal is reduced to less than half of the initial value by addition of at least one further partial amount of the transition metal complex.

3. The process as claimed in claim 2, wherein the initial molar ratio ratio of aluminum:transition metal is greater than 100.

4. The process as claimed in claim 1, wherein the transition metal is chromium.

5. The process as claimed in claim 1, wherein said transition metal is complexed with a polydentate nitrogen containing complexing ligand.

6. The process as claimed in claim 5, wherein the complexing ligand comprises a 1,3,5-triazacyclohexane or 1,4,7-triazacyclononane skeleton.

7. The process as claimed in claim 5, wherein the alkylaluminoxane is methylaluminumoxane.

8. The process as claimed in claim 1, wherein the oligomerization is conducted at a temperature ranging from 0 to 120° C.

9. The process as claimed in claim 1, wherein the oligomerization is conducted in an aliphatic hydrocarbon, halogenated hydrocarbon or aromatic hydrocarbon solvent.

10. The process as claimed in claim 1, wherein the oligomerization is conducted with an α-olefin having at least three carbons atoms.

11. The process as claimed in claim 1, wherein the oligomerization is conducted at a pressure ranging from ambient to 120 bar.

* * * * *